(12) United States Patent
Pecora

(10) Patent No.: US 9,993,310 B2
(45) Date of Patent: Jun. 12, 2018

(54) SURGICAL DRAPE WITH SLEEVE AND FENESTRATION

(71) Applicant: Michael John Pecora, Pittsburgh, PA (US)

(72) Inventor: Michael John Pecora, Pittsburgh, PA (US)

( * ) Notice: Subject to any disclaimer, the term of this patent is extended or adjusted under 35 U.S.C. 154(b) by 987 days.

(21) Appl. No.: 14/330,435

(22) Filed: Jul. 14, 2014

(65) Prior Publication Data

US 2016/0008072 A1    Jan. 14, 2016

(51) Int. Cl.
*A61B 46/27* (2016.01)
*A61B 46/00* (2016.01)
*A61B 46/20* (2016.01)

(52) U.S. Cl.
CPC .............. *A61B 46/00* (2016.02); *A61B 46/27* (2016.02); *A61B 2046/205* (2016.02)

(58) Field of Classification Search
CPC ....... A61B 19/08; A61B 19/088; A61B 46/20; A61B 46/27; A61B 46/13; A61B 2046/201; A61B 2046/205; A61B 46/00; A41D 13/1236; A41D 13/1245; A41D 13/1272; A41D 13/1263; A41D 13/1281
USPC ............................... 128/849–855, 856; 2/114
See application file for complete search history.

(56) References Cited

U.S. PATENT DOCUMENTS

| | | | | |
|---|---|---|---|---|
| 4,550,724 A | * | 11/1985 | Berrehail | A61F 5/3746 128/874 |
| 4,730,609 A | * | 3/1988 | McConnell | A61B 46/00 128/853 |
| 4,890,628 A | | 1/1990 | Jackson | |
| 5,975,082 A | | 11/1999 | Dowdy | |
| 7,316,233 B2 | * | 1/2008 | Auerbach | A61B 46/27 128/849 |
| 8,100,130 B2 | | 1/2012 | Allen | |

(Continued)

FOREIGN PATENT DOCUMENTS

JP        Heisei 16 A    7/2004
          2004-188058

OTHER PUBLICATIONS

International Searching Authority; International Search Report and Written Opinion of the International Searching Authority; International Application No. PCT/US 15/39945; Patent Cooperation Treaty; pp. 1-10; publisher United States International Searching Authority; Published Alexandria, Virginia, US; copyright and dated Dec. 4, 2015; (10 pages).

(Continued)

*Primary Examiner* — Kari Rodriquez
*Assistant Examiner* — Camtu Nguyen
(74) *Attorney, Agent, or Firm* — Metz Lewis Brodman Must O'Keefe LLC

(57) ABSTRACT

A surgical drape is provided that has a drape body that has an upper surface and an oppositely disposed lower surface. A sleeve extends from the drape body into which an arm of a patient is located when the drape is positioned on the patient. A sleeve attachment component is located on the sleeve, and a body attachment component that is located on the drape body. The sleeve attachment component is attachable to the body attachment component in order to attach the sleeve to the drape body at a first location. A fenestration is present through which a portion of the patient can be accessed when the drape is positioned on the patient.

13 Claims, 4 Drawing Sheets

(56) References Cited

U.S. PATENT DOCUMENTS

| | | | |
|---|---|---|---|
| 8,863,747 B1* | 10/2014 | Stephenson | A61B 46/00 128/849 |
| 2003/0188753 A1 | 10/2003 | Jascomb | |
| 2005/0279366 A1 | 12/2005 | Adragna | |
| 2008/0047567 A1 | 2/2008 | Bonutti | |
| 2010/0031966 A1 | 2/2010 | Allen | |
| 2010/0275377 A1 | 11/2010 | West | |
| 2011/0083244 A1* | 4/2011 | Gellerstedt | A41D 13/1209 2/59 |
| 2012/0097175 A1 | 4/2012 | Allen | |
| 2012/0298115 A1 | 11/2012 | Haines | |

OTHER PUBLICATIONS

Almany, Steven L; Radial artery Access for Diagnostic and Interventional Procedures; 1999, pp. 1-17; Publisher—Accurned Systems, Inc.; Ann Arbor, MI, USA; Copyright 1999; (17 pages).

Rao, Sunil V., Trends in the Prevalence and Outcomes of Radial and Femoral Approaches to Percutaneous Coronary Intervention, JACC: Cardiovascular Interventions: 2008, pp. 379-386; American College of Cardiology Foundation; (7 pages).

Speiser, Bernadette; title: Tips When Prepping for Radial Procedures; website http://www.dicardiology.com/article/tips-when-prepping-radial-procedures; visited Sep. 23, 2014; copyright 2011; Publisher—DAIC Diagnostic and Interventional Cardiology; Arlington Heights, Illinois, USA; (6 pages).

Iverson, Angela; title: Choosing Tools for Transradial Procedures: website http://www.dicardiology.com/article/choosing-tools-transradial-procedures; visited Sep. 23, 2014; copyright 2011; Publisher—DAIC Diagnostic and Intervetional Cardiology, Arlington Heights, Illinois, USA; (5 pages).

Ecolab; title: Combination Femoral and Transradial Surgical Patient Drapes; website http://www.ecolab.com/product/combination-access-angioplasty-patient-drapes/; visited Sep. 23, 2014; copyright 2014; Publisher—Ecolab Inc. / Microtek Medical Inc.; Columbus, Mississippi, USA; (6 pages).

Schussler, Jeffrey; title: Trends and Advances in Transradial Access: Highlights for the SCAI 2013 Scientific Session; website http://www.editiondigital.net/display article.php?id=1496996; visited Sep. 23, 2014; copyright 2013; Publisher—Diagnostic and Interventional Cardiology; Arlington Heights, Illinois, USA; (2 pages).

Karrowni, Wassef; title: Radial Versus Femoral Access for Primary Percutaneous Interventions in ST-Segment Elevation Myocardial Infraction Patients; JACC: Cardiovascular Interventions; 2013: pp. 814-823; vol. 6, issue No. 8; Publisher—Elsevier, Inc.: Duram, North Carolina, USA; Copyright 2013 The America Collee of Cardiology Foundation; (10 pages).

Jolly, Sanjit S; title: Radial versus femoral access for coronary angiography and intervention in patiens with actue coronary syndromes (RIVAL): a randomised, parallel group, multicenter trial; The Lancet; 2011; summary of pp. 1409-1420; vol. 377, Issue 9775; Published—The Lancet; London, United Kingdom; Copyright 2011 The Lancet; (2 pages).

Kern, Morton; title: The Armen Glove for Radial Access Prep—A Better Way; website http://www.cathlabdigest.com/articles/The-Armen-Glove-Radial-Access-Prep-%E2%80%93-A-Better-Way; visited Oct. 13, 2014; copyright 2010; Publisher Cath Lab Digest, vol. 18—Issue 5; Malvern, Pennsylvania, USA; (6 pages).

* cited by examiner

SURGICAL DRAPE WITH SLEEVE AND FENESTRATION

FIELD OF THE INVENTION

The present invention relates generally to a surgical drape for use during a surgical procedure to maintain a sterile environment that includes a sleeve into which an arm of the patient is positioned and a fenestration through which surgical instruments or access to the patient can be achieved. More particularly, the present application relates to a surgical drape that has two arms that are attachable to a drape body, and four fenestrations that may provide access to radial and femoral blood vessels.

BACKGROUND

Sterile drapes are used during medical procedures to maintain a sterile field which can be used by the medical operator during a medical procedure to prevent contamination of the site upon or through which the operator performs the procedure. The drape maintains an effective barrier that minimizes or prevents the passage of microorganisms between the sterile and non-sterile fields. The drape should be resistant to blood and aqueous fluid. Sterile drapes are generally made of a water repellent or water-impermeable material, or are coated with such a material. Sterile drapes commonly contain one or more openings (fenestrations) through which the procedure is performed. The drapes commonly used during angiography and cardiac catheterization procedures include access site fenestrations to allow access to the left or right femoral arteries. These fenestration sites can be situated over the femoral arteries, and then affixed to the skin along the outer edges of the fenestrations to secure and maintain the position of the drape relative to the access site during the procedure.

Cardiac catheterization and angiography procedures are medical procedures which are generally performed from femoral (groin) access sites, and more recently from radial (wrist) artery access sites. A sterile drape is situated with the appropriate fenestration site secured over the chosen arterial access site. An arterial access sheath is introduced through the fenestration into the appropriate artery. The sheath then permits introduction of arterial catheters or tubes, which in turn allows introduction of X-ray contrast dye and equipment through catheters to the organ being investigated or treated.

Four common options for cardiac catheterization angiography access sites (arterial catheterization) are currently available and may be selected depending upon the individual patient, medical procedure to be performed, and preference of the operator. Access through the right femoral artery is the most commonly used and catheter designs are geared for this approach. Access through the left femoral artery may be used if the right femoral artery is not available. The third is right radial artery access. This approach is becoming more popular because of a significant decrease in vascular risk to the patient from this approach. However, access through the right radial artery is more time consuming and technically challenging for the operator. The fourth, and least common approach, is through the left radial artery.

The radial approach has been gaining popularity over the past 10-20 years because of potential advantages in patient comfort, procedural costs, procedural complications, major and minor complications, and length of stay. Relative to the femoral approach, a radial artery catheterization strategy has been estimated to reduce major bleeding from 6.1% to 2.7% of catheterization procedures and to reduce major vascular complications from 0.45% to 0.16% of catheterization procedures. However, once a sterile drape is applied 2-5% of procedures attempted from the radial approach cannot be completed in this manner, necessitating a switch in the preparation by the staff, in mid procedure, from draping the radial arterial area to the femoral arterial area, which lengthens procedural time.

Despite the continued growth in radial artery procedures performed, no single approach is universally adopted in any center or by any single cardiologist. Therefore, any technical improvements in catheterization pre-procedural set-up which assist in a more universal approach could save time, could improve profitability, and could reduce procedural complications.

During a medical procedure, it may be the case that the arms of a patient may move thus potentially causing the surgical drape to move out of position thus jeopardizing the sterile field. Further, the arms of the patient may not be in a comfortable or convenient position for the patient or for the health care provider during use of the surgical drape. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which.

Figure 1:
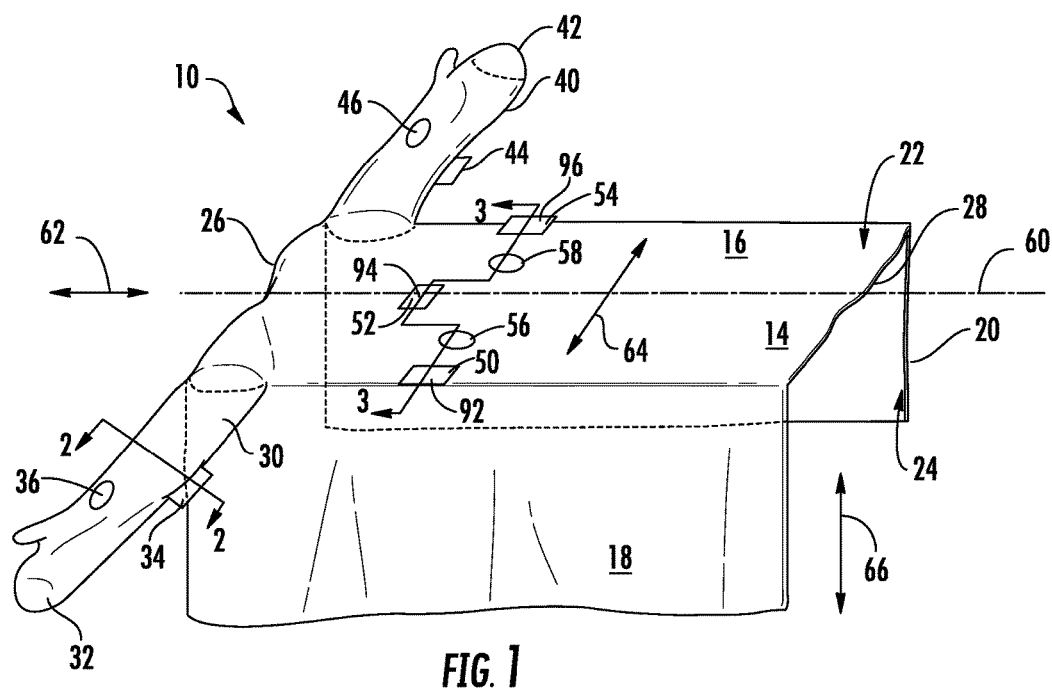
FIG. 1 is a perspective view of a surgical drape in accordance with one exemplary embodiment.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for a surgical drape 10 that can be donned by a patient 12 during a health care procedure that features multiple fenestrations 36, 46, 56 and 58 to provide access to various areas of the patient 12 as desired for conducting the surgical procedure. The drape 10 has a right sleeve 30 and a left sleeve 40 into which arms 70, 76 of the patient 12 can be positioned when the surgical drape 10 is positioned onto the patient 12. The sleeves 30, 40 include sleeve attachment components 34, 44 that are attachable to various body attachment components 50, 52, 54 that are located on a drape body 14 of the drape 10 that may cover the torso and legs of the patient 12. The sleeves 30, 40 can thus be attached at different locations on the drape body 14 so that the arms 70, 76 can likewise be arranged at different locations and positions as desired during the surgical procedure. The attachment may be robust enough to securely hold the arms 70, 76 in the desired positions, and the attachment may be effected with releasable fasteners so that the sleeves 30, 40 can be moved to different locations and positions multiple times during the surgical procedure as needed. The surgical drape 10 can be used in connection with any type of surgical procedure. For example, the surgical drape 10 may be used in surgical procedures related to cardiology and angiography.

One exemplary embodiment of the surgical drape 10 is shown with reference to FIG. 1. The surgical drape 10 has a drape body 14 that can be used to cover a torso and legs of a patient 12 during a surgical procedure. The drape body 14 has a forward edge 26 and a rearward edge 28 that is oppositely disposed from the forward edge 26 in a longitudinal direction 62. The forward edge 26 may be located at the neck of the patient 12 when the drape 10 is positioned onto the patient 12. The rearward edge 28 may extend over and cover the feet of the patient 12. However, it is to be understood that the forward and rearward edges 26, 28 may be arranged in different manners and may extend different lengths in accordance with other versions of the surgical drape 10. The drape body 14 has a central portion 16, right portion 18 and left portion 20. The central portion 16 may extend such a degree in a lateral direction 64, that is perpendicular to the longitudinal direction 62, that it covers the patient 12 on both the left and right side of the patient 12. The right and left portions 18, 20 may function to cover the right and left sides of the patient 12 in some arrangements, and may extend to such lengths in the lateral and height directions 64, 66 that they function to cover areas of the surgical site that are not the patient 12 to further ensure that a sterile field is maintained during the healthcare procedure. The drape body 14 covers the torso of the patient 12 and may extend in the longitudinal direction 62 past the feet of the patient 12 and past an end of the catheterization table. The drape body 14 along with other portions of the surgical drape 10 provide for a sterile platform for placement of equipment during a catheterization procedure. The drape body 14 may be of any shape and may have varying dimensions. The drape body 14 may be provided as a rectangular shaped component and sized to cover at least a majority of the patient's 12 body during the surgical procedure.

The drape body 14 may be made of a single piece of material or may be made of multiple types of material or different components that are attached to one another. The drape body 14 may be a single layer or may include multiple layers made of the same or different materials. The drape body 14 may have an upper surface 22 and an oppositely disposed lower surface 24. The drape body 14 may be arranged so that there are no pockets or other hollow portions into which any portion of the patient 12 is disposed when the surgical drape 10 is positioned onto the patient 12. The lower surface 24 may engage the patient 12 and the upper surface 22 may face in a direction opposite from the patient 12 and not engage the patient 12 when the surgical drape 10 is worn. An additional layer of sterile drape may be used to facilitate sterile coverage of non-sterile areas beneath the left 40 and/or right 32 sleeves 40, 30/arms 76, 70 of drape/patient 10/12.

Figure 2:
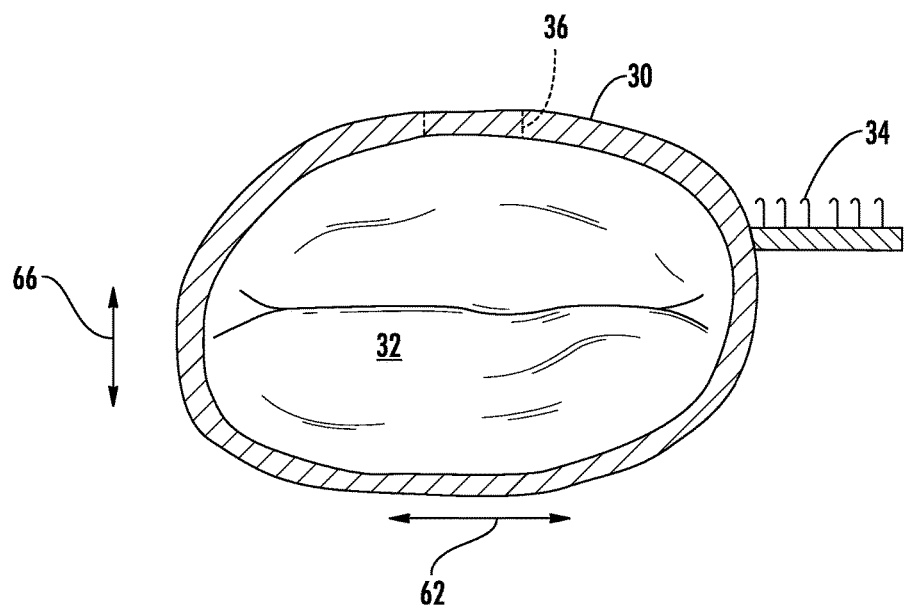
FIG. 2 is a cross-sectional view taken along line 2-2 of FIG. 1.

The right sleeve 30 extends from the drape body 14 and is provided so that the right arm 70 of the patient 12 can be positioned therein. A proximal terminal end of the right sleeve 30 may engage the drape body 14 at a location that demarcates the boundary between the central portion 16 and the right portion 18. The right sleeve 30 may engage the forward edge 26 or may be spaced some distance from the forward edge 26 in the longitudinal direction 62. With reference to FIG. 2, the right sleeve 30 forms a pocket that can completely surround the right arm 70 when positioned within the right sleeve 30 along a length of the right sleeve 30 that extends away from the drape body 14. With reference back to FIG. 1, this pocket may extend from the point of engagement with the drape body 14 all the way to the terminal end of a right mitten 32 that may likewise be closed. However, it is to be understood that in accordance with other exemplary embodiments that the right sleeve 30 need not have a pocket that extends all the way from the drape body 14 to the terminal end of the right mitten 32. For example, the right sleeve 30 may be open along its entire length on its bottom side such that no surrounding pocket at any location at all in the right sleeve 30 is present.

The right sleeve 30 has a right mitten 32 located at the terminal end of the right sleeve 30. The right mitten 32 may completely contain the right hand 72 of the patient 12 to help achieve a sterile field while working closely with the hand 72 of the patient 12 during the surgical procedure. The right sleeve 30 may include a right sleeve attachment component 34 that can be used to attach the right sleeve 30 to the drape body 14. The right sleeve attachment component 34 is shown as extending from an outer surface of the right sleeve 30. In other embodiments, the right sleeve attachment component 34 may be attached to an inner surface of the right sleeve 30. The right sleeve attachment component 34 may be buttons, snaps, hooks, adhesive, magnets, or hook and loop type fastener in accordance with various exemplary embodiments. In one arrangement of the surgical drape 10, the right sleeve attachment component 34 are hooks of a hook and loop type fastener. The right sleeve attachment component 34 may be arranged for permanent attachment to the drape body 14 so that once attached, the right sleeve attachment component 34 is not removable from the drape body 14. However, other exemplary embodiments exist in which the attachment is releasable attachment such that the right sleeve attachment component 34 can be attached to and removed from the drape body 14 a multiple number of times as desired.

The right sleeve 30 may have a right sleeve fenestration 36 that may extend through the outer surface of the right sleeve 30 to the inner surface of the right sleeve 30 to in effect allow the pocket of the right sleeve 30 to be accessed. The right sleeve fenestration 36 may be arranged so that it does not extend completely through the right sleeve 30. In this regard, the right sleeve fenestration 36 may not extend through the outer surface twice and the inner surface twice. Instead, the right sleeve fenestration 36 may only extend through the outer surface once and the inner surface once, leaving the right sleeve 30 opposite to the right sleeve fenestration 36 solid. However, in other arrangements the right sleeve fenestration 36 may in fact extend completely through the right sleeve 30 so that it extends through the outer surface twice and the inner surface twice. There may be multiple right sleeve fenestrations 36 in other arrangements of the surgical drape 10, or a single right sleeve fenestration 36 may be present. The right sleeve fenestration 36 may be variously shaped. For example, the right sleeve fenestration 36 may be oval shaped, rectangular shaped, square shaped, triangular shaped, or circular in shape in accordance with various exemplary embodiments.

The surgical drape 10 has a left sleeve 40 that extends from the drape body 14 at a location opposite from the right sleeve 30 in the lateral direction 64. The left sleeve 40 may have a left mitten 42 located at its terminal end, a left sleeve attachment component 44, and a left sleeve fenestration 46. The left sleeve 40 may form a pocket that completely surrounds a left arm 76 of the patient 12 along a portion of the length of the left sleeve 40 that extends away from the drape body 14.

The left sleeve 40, left mitten 42, left sleeve attachment component 44, and left sleeve fenestration 46 may be arranged and configured in manners similar to the right sleeve 30, right mitten 32, right sleeve attachment component 34, and right sleeve fenestration 36 as previously described and a repeat of this information is not necessary. The manners similar to one another may be identical in nature or the sleeves 30, 40 and their components may be different from one another but are arranged as previously described. Further, the right and left sleeves 30, 40 and their accompanying components may be provided in different manners from one another in accordance with various exemplary embodiments. For example, in one arrangement of the surgical drape 10, the right sleeve fenestration 36 may be rectangular in shape, while the left sleeve fenestration 46 is oval in shape. In yet another arrangement of the surgical drape 10, the right sleeve 30 may include a right sleeve attachment component 34 and a right mitten 32, and the left sleeve 40 may be provided without a left sleeve attachment component 44 and without a left mitten 42. Although the right and left sleeve fenestrations 36, 46 can be located at any portion of the right and left sleeves 30, 40, the fenestrations 36, 46 may be positioned at the distal ends of the sleeves 30, 40. The right sleeve attachment component 34 and left sleeve attachment component 44 may be positioned on the right and left sleeves 30, 40 so that they are located proximate to the wrists of the patient 12. The right and left sleeve fenestrations 36, 46 may be positioned to allow for access to the brachial arteries or antecubital veins of the right and left arms 70, 76 of the patient 12.

Figure 3:
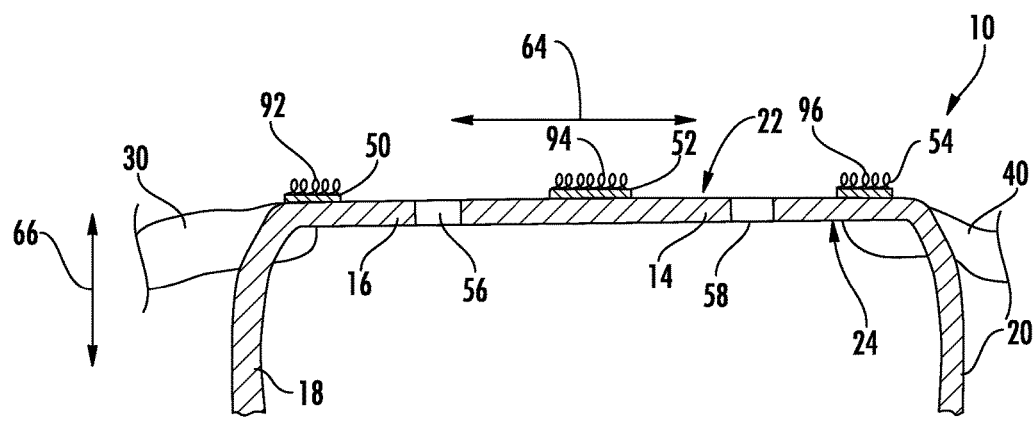
FIG. 3 is a partial cross-sectional view taken along line 3-3 of FIG. 1.

The right and left sleeve attachment components 34 and 44 may be attached to first, second and third body attachment components 50, 52 and 54 that are carried by the drape body 14. With reference to FIGS. 1 and 3, the first body attachment component 50 may be located on the upper surface 22 of the drape body 14 in the central portion 16 on the right side of a centerline 60 of the surgical drape 10. The first body attachment component 50 may be located at an edge of the central portion 16 and adjacent the right portion 18. In other exemplary embodiments, the first body attachment component 50 may be at any location on the portions 16, 18 and/or 20 and may be on the upper and/or lower surfaces 22, 24.

The second body attachment component 52 may be located on the upper surface 22 of the central portion 16 at the centerline 60. The third body attachment component 54 may likewise be located on the upper surface 22 of the central portion 16 but on the left side of the centerline 60 opposite to that of the first body attachment component 50 in the lateral direction 64. As with the first body attachment component 50, the second and third body attachment components 52 and 54 may be at other locations on the portions 16, 18 and/or 20 and may be on the upper and/or lower surfaces 22, 24 in other exemplary embodiments. The attachment components 34 and 44 may have less area than the corresponding body attachment components 50, 52 and 54. The sleeve attachment components 34, 44 can be located at various portions of the body attachment components 50, 52 and 54 along their respective lengths.

The surgical drape 10 may also include a right femoral blood vessel fenestration 56 and a left femoral blood vessel fenestration 58. The right femoral blood vessel fenestration 56 may be located at the central portion 16 spaced from the centerline 60 in the lateral direction 64 a distance that is not as great as the distance from the first body attachment component 50 to the centerline 60 in the lateral direction 64. The left femoral blood vessel fenestration 56 may be located at the central portion 16 spaced from the centerline 60 in the opposite direction in the lateral direction 64 from the right femoral blood vessel fenestration 56. The left femoral blood vessel fenestration 56 may be spaced a distance from the centerline 60 that is less than the distance from the centerline 60 to the third body attachment component 54 in the lateral direction 64. The fenestrations 56 and 58 may extend completely through the central portion 16 from the upper surface 22 to the lower surface 24.

The fenestrations 56 and 58 may be variously shaped. For example, the fenestrations 56, 58 may be rectangular, square, oval, circular, or triangular in shape in accordance with various exemplary embodiments. The fenestrations 56 and 58 need not be located on opposite sides of the centerline 60, but may be located on the same side of the centerline 60 in other exemplary embodiments. Although disclosed as being located at the central portion 16, the fenestrations 56 and 58 may be in the right portion 18 and/or left portion 20 in other versions of the surgical drape 10. Still further, although a pair of fenestrations 56 and 58 are shown, it is to be understood that from 0-10 fenestrations may be present in the drape body 14 in other arrangements.

Figure 4:
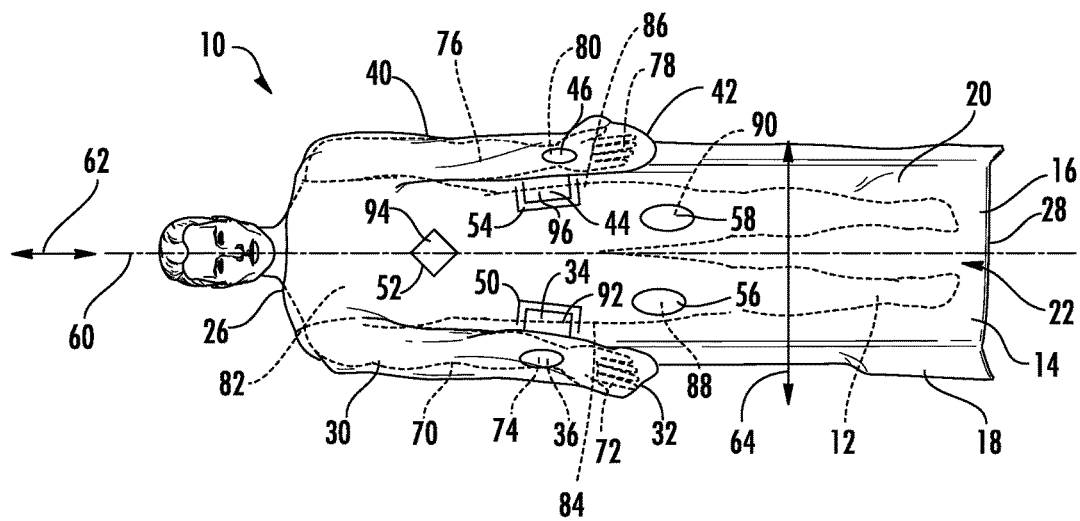
FIG. 4 is a top view of the surgical drape of FIG. 1 positioned on a patient with the right and left sleeves attached at first and third positions to the drape body.

FIG. 4 shows the surgical drape 10 positioned onto the patient 12. The drape body 14 extends from the neck of the patient 12 past the feet of the patient 12 in the longitudinal direction 62. The right femoral blood vessel fenestration 56 is located above the right femoral artery 88 of the patient 12. The right femoral artery 88 can thus be accessed if desired by the health care provider during the surgical procedure. In a similar manner, the left femoral blood vessel fenestration 58 is located above the left femoral artery 90 of the patient 12 to allow the health care provider to access this artery 90 if needed. Although described as accessing the right and left femoral arteries 88, 90 the right and left femoral blood vessel fenestrations 56 may be used to access other blood vessels or portions of the patient 12, such as the left or right femoral veins, in accordance with other exemplary embodiments.

The central portion 16 of the drape body 14 overlays the torso 82 of the patient 12, and the second body attachment component 52 is positioned at a location that is above the torso 82 of the patient 12 in the height direction 66. The second body attachment component 52 could be located above the chest or abdomen in some embodiments. The first body attachment component 50 is located at a first location 92 that is proximate to a right hip 84 of the patient 12. In other embodiments, the first location 92 need not be at a location that proximate to the right hip 84 but could be proximate to various parts of the patient's body 12. The third body attachment component 54 is at a third location 96 proximate to a left hip 86 of the patient 12. Attachment of the left sleeve 40 to the third location 96 may allow for the left sleeve 40 and left arm 76 to be positioned along the left hip 86 and out of the way in the event that another one of the access sites 36, 56 or 58 is chosen for the procedure. Attachment of the right sleeve 30 to the first body attachment component 50 so that the right sleeve 30 and the right arm 70 are positioned at the first location 72 along the right hip 84 may provide for a convenient position for the sleeve 30 and arm 70 regardless of the access site 36, 56, 58 or 46 chosen for the procedure.

The right arm 70 is positioned within the right sleeve 30, and the right hand 72 is within the right mitten 32. In a similar manner, the left arm 76 is within the left sleeve 40, and the left hand 78 is inside of the left mitten 42. The arms and hands, 70, 72, 76 and 78 are covered by the surgical drape 10 in order to maintain a sterile field. The right sleeve attachment component 34 is attached to the first body attachment component 50 in order to attach the right sleeve 30 to the drape body 14 at the first location 92. The right sleeve 30 and the right arm 70 extend in the longitudinal direction 62 of the surgical drape 10 and are located along the right side of the patient 12. The attachment of components 34 and 50 provides a secure fixing of the right arm 70 in place during the surgical procedure. The right sleeve fenestration 36 is positioned above a right radial artery 74 of the patient 12 in the height direction 66. The right radial artery 74 may be accessed by the health care provider during the surgical procedure through the right sleeve fenestration 36. Alternatively, the right radial artery 74 need not be accessed during the surgical procedure. However, the right arm 70 can still be placed at the first location 92 during the surgical procedure through engagement of the attachment components 34 and 50 for comfort reasons of the patient 12, or to provide known and secure positioning of the right arm 70 during the surgical procedure to help ensure a sterile field is maintained.

The left arm 76 is located within the left sleeve 40, and the left hand 78 is positioned within the left mitten 42. These portions 76, 78 of the patient 12 are likewise contained by the surgical drape 10 to achieve sterility during the surgical procedure. The left sleeve attachment component 44 engages the third body attachment component 54 to cause the left arm 76 and the left sleeve 40 to be located at the third location 96. The left arm 76 and left sleeve 40 extend along the left side of the patient 12 in the longitudinal direction 62. The attachment of components 44 and 54 provides secure and known positioning of the left arm 76 during the surgical procedure. The left sleeve fenestration 46 is located above a left radial artery 80. The health care provider may access the left radial artery 80 as desired when performing the surgical procedure through the left sleeve fenestration 46. Again, it is not necessary for the left radial artery 80 to be accessed during the surgical procedure even though the left arm 76 is located at the third location 96. This positioning of the left arm 76 with respect to the drape body 14 may afford comfort to the patient 12, and may provide a known and convenient location for the left arm 76 to be maintained during the surgical procedure to make the health care procedure easier to perform and to help achieve a sterile field.

Although described as being used to access the right and left radial arteries 74 and 80, the right and left sleeve fenestrations 36 and 46 need not be used to access these arteries 74 and 80 in other embodiments. For example, the fenestrations 36, 46, or other fenestrations in the sleeves 30, 40 may be used to access other portions of the right and left arms 70, 76 of the patient 12 as desired.

Figure 5:
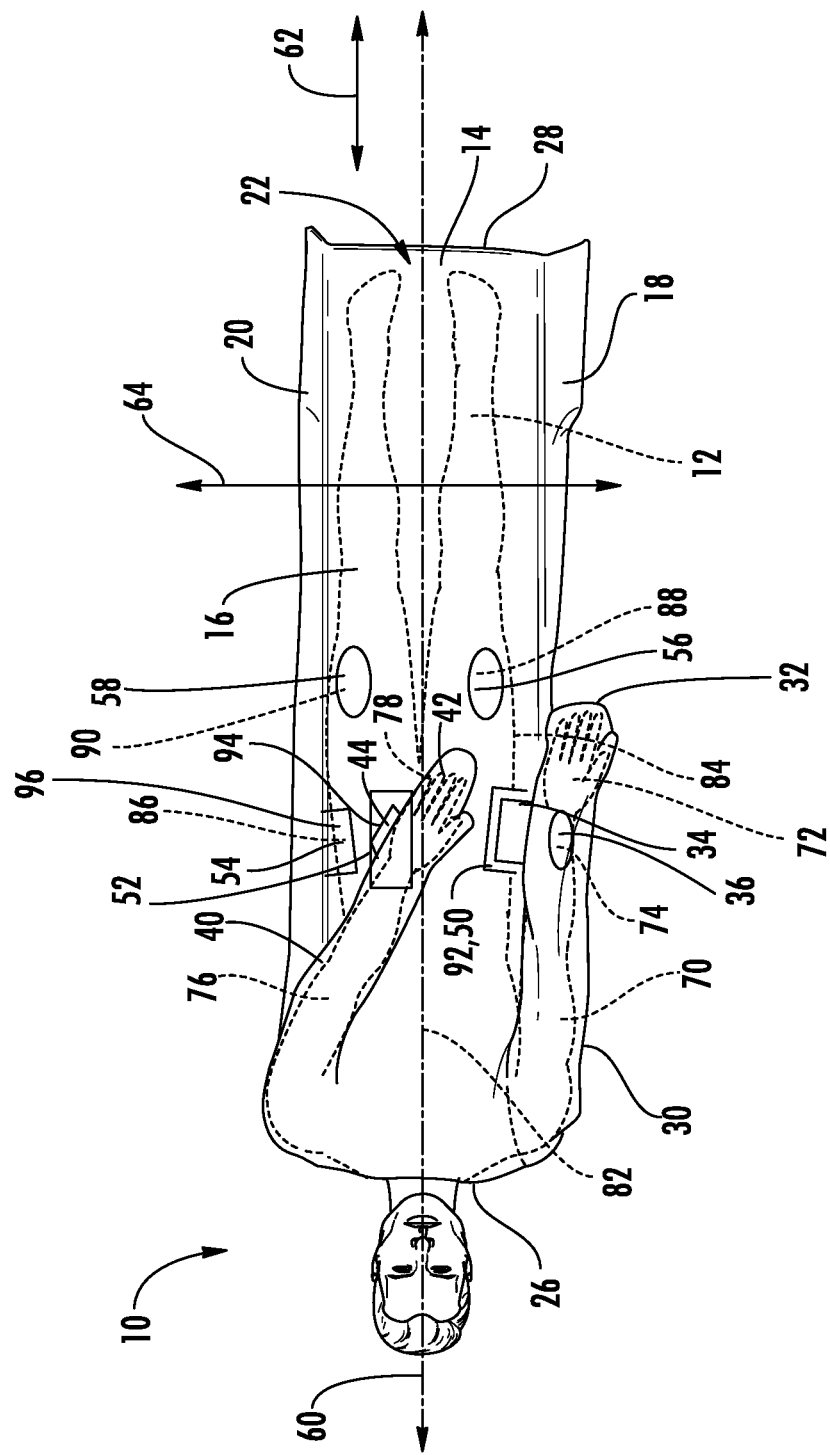
FIG. 5 is a top view of the surgical drape of FIG. 1 positioned on the patient with the right and left sleeves attached at first and second positions to the drape body.

FIG. 5 shows the surgical drape 10 positioned onto the patient 12 and arranged in a manner different than that shown with respect to FIG. 4. Here, the right arm 70 and right sleeve 30 are arranged in the same manner as that of FIG. 4 such that they lay along the right side of the patient 12 and are attached to the first body attachment component 50 at the first location 92. The left sleeve 40 and left arm 76 are removed from the third body attachment component 54 at the third location 96 and are repositioned with respect to the drape body 14. This positioning may be done in order to provide comfort to the patient 12 or to place the left arm 76 into a more convenient position during the surgical procedure. The left sleeve attachment component 44 is engaged with the second body attachment component 52 and is held thereon in order to likewise hold the left sleeve 40 and left arm 76 to the drape body 14 at the second location 94. The left sleeve 40 and left arm 76 are extended across the chest/torso 82 of the patient with the elbow of the left arm 76 extended or slightly flexed.

Attachment of one of the sleeves 40, 30 to the second body attachment component 52 at the second location 94 may cause the arms 70 or 76 to be attached to the mid-torso of the drape body 14 so that the arm 70 or 76 is supported similar to the support of the arm 70 or 76 with a slant. This support may allow for comfortable, supported, stable and sterile position of the arm 70 or 76 throughout the procedure.

The engagement between the second body attachment component 52 and the left sleeve attachment component 44 maintains the left arm 76 and left sleeve 40 securely in position such that they will not move until they are disengaged by the healthcare provider. The left sleeve 40 and left arm 76 extend for some distance in the longitudinal direction 62 and are slanted so as to extend some distance in the lateral direction 64 from the shoulder down towards the left hand 78. As such, the right sleeve 30 and left sleeve 40 are arranged in FIG. 5 so that one of them extends a greater distance in the longitudinal direction 62 than the other, and so that one of them extends a greater distance in the lateral direction 64 than the other.

The positioning of the third body attachment component 54 and the length of the left sleeve 40 and position of the left sleeve attachment component 44 may be arranged such that the left sleeve attachment component 44 cannot be engaged with the first body attachment component 50 to place the left sleeve 40 at the first location 92. In a similar manner, the length of the right sleeve 30 along with the positioning of the right sleeve attachment component 34 may be made such that it is impossible for the right sleeve attachment component 34 to engage and be attached to the third body attachment component 54 at the third location 96. However, these arrangements need not be made in other versions of the surgical drape 10.

The right sleeve attachment component 34 and the left sleeve attachment component 44 may be arranged so that they are hooks of a hook and loop type fastener that are located on both the tops and bottoms of the portion of the components 34 and 44 extending from the sleeves 30 and 40. With reference to FIG. 2, the right sleeve attachment component 34 include hooks that are only on the top and not the bottom surface of the portion of the right sleeve attachment component 34 extending from the right sleeve 30. Placement of the hooks on both the top and bottom may afford additional comfort, utility to the surgical drape 10 as shown in FIG. 5 because the arms 70, 76 can be positioned in variable ways to allow for the palms to be located facing up or facing down, and for other portions of the arms 70, 76 to be facing different directions. The right arm 70 is laying palm facing up, while the left arm 76 if laying palm facing down. However, other arrangements are possible in which the hooks are only on the top or bottom surfaces, and in which the drape 10 can be bunched up or twisted to accommodate the engagement between the attachment components 34, 44 and the body attachment components 50, 52 and 54.

Figure 6:
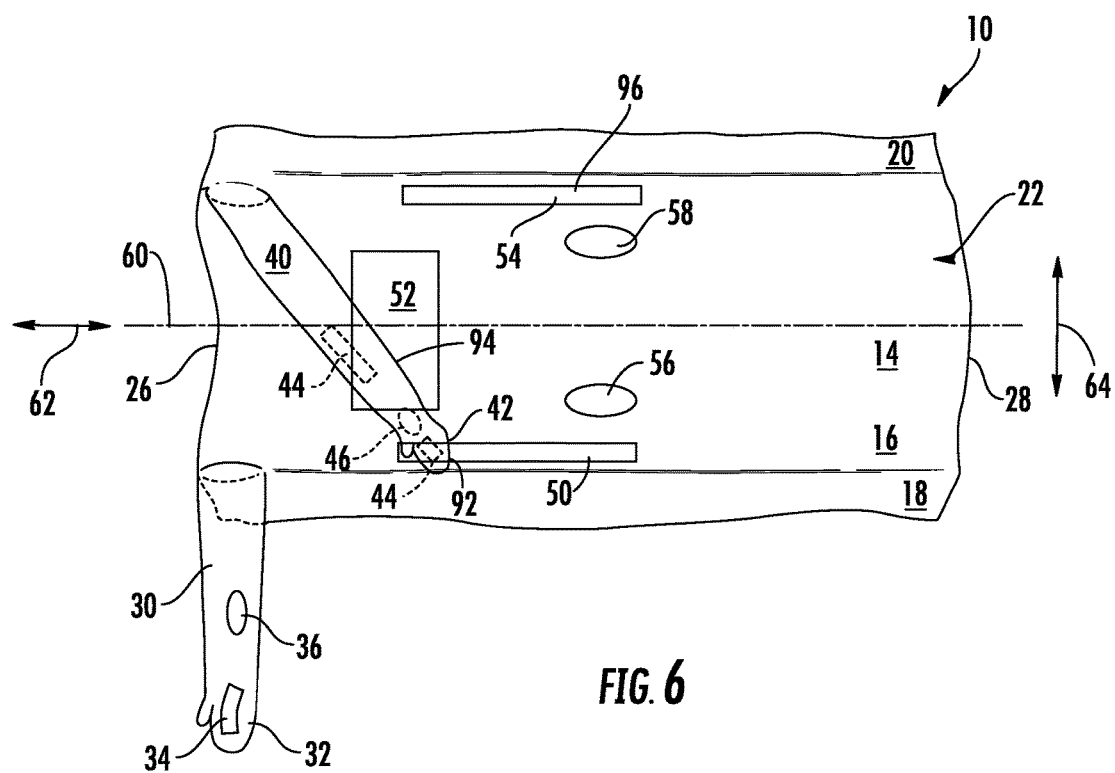
FIG. 6 is a top view of a surgical drape in accordance with another exemplary embodiment.

An alternative exemplary embodiment of the surgical drape 10 is illustrated in FIG. 6. The fenestrations 36, 46, 56 and 58 are arranged in a similar manner as those previously discussed. However, the attachment configurations of the left and right sleeves 40, 30 are different. The right sleeve attachment component 34 is attached to an outer surface of the right mitten 32 of the right sleeve 30. The right sleeve attachment component 34 lays completely on the outer surface of the right mitten 32 and no portion of the lower surface of the right sleeve attachment component 34 extends off of the outer surface of the right mitten 32 or other portion of the right sleeve 30. The left sleeve attachment component 44 is likewise configured so that it lays on the left sleeve 40 and left mitten 42 without having any portion of its lower surface extending off of the outer surfaces of these components. Further, the left sleeve attachment component 44 is broken up into two separate components that are on either side of the left sleeve fenestration 46 and are both of different sizes. A first portion of the left sleeve attachment component 44 is located on the left mitten 42, and a second portion of the left sleeve attachment component 44 is longer than the first disclosed portion and is located approximately at the left elbow of the left arm 76.

The body attachment components, 50, 52 and 54 are configured differently than those previously disclosed. The first and third body attachment components 50, 54 are rectangular in shape and are narrow and extend along a greater length in the longitudinal direction 62 than the lateral direction 64. The second body attachment component 52 is rectangular in shape and extends in a greater distance in the lateral direction 64 than in the longitudinal direction 62 with respect to the other two body attachment components 50, 54. The body attachment components, 50, 52 and 54 may be made out of a hook and loop type fastener component, such as loops. In this regard, the entire areas of the body attachment components 50, 52, 54 may be made out of loops of a hook and loop type fastener. The body attachment components 50, 52 and 54 may be permanently attached to the upper surface 22 of the central portion 16 through adhesive, sewing, sonic welding, mechanical fasteners, or any other type of attachment mechanism.

The right sleeve 30 and right arm 70 do not engage the drape body 14 and are not attached thereto beyond the proximal terminal end of the right sleeve 30. The left sleeve 40 and left arm 76 extend across the torso 82 of the patient 12 and are attached to the drape body 14. In this regard, the first portion of the left sleeve attachment component 44 located at the left mitten 42 engages and is attached to the first body attachment component 50 in order to place the left sleeve 40 and left hand 78 at the first location 92. Additional portions of the left sleeve attachment component 44 engage the second body attachment component 52 so as to place the left sleeve 40 and left arm 76 at the second location 94. All of the left sleeve attachment component 44 can be made of hooks of the hook and loop type fastener so as to engage the body attachment components 50, 52, 54 as needed. Although not explicitly shown in FIG. 6, the left sleeve attachment component 44 can engage the third body attachment component 54 in order to place the left sleeve 40 and left arm 76 at the third location 96. Also, although not shown specifically in FIG. 6, the right sleeve 30 and right arm 70 may be located at any one of the three locations 92, 94 and 96 through attachment of the right sleeve attachment component 34 to the various body attachment components 50, 52 and 54.

The surgical drape 10 can be arranged so that the right sleeve 30 and left sleeve 40 are located at the first location 92 at the same time. Likewise, the right and left sleeves 30, 40 may be arranged with the surgical drape 10 so that they can be simultaneously located at the second location 94, or simultaneously located at the third location 96 in accordance with various exemplary embodiments. As such, the right and left sleeves 30, 40 may be positionable at various locations on the drape body 14 in order to provide for patient comfort and to help maintain the sterile field during the surgical procedure.

The mechanisms of attaching the sleeves 30, 40 to the drape body may be varied from those explicitly disclosed. For example, the entire upper surface 22 of the drape body 14 may be made of a material such as loops of a hook and loop type fastener. The sleeve attachment components 34, 44 may be arranged as previously discussed or could be located along the entire outer surfaces of the right and left sleeves 30, 40. The right and left sleeves 30, 40 may be attached to various portions of the drape body 40 so that they and the right and left arms 70, 76 can be placed in various locations and positions with respect to the drape body 14. The first, second and third body attachment components 50, 52 and 54 may be thought of as different locations on the drape body 14 if the loop material extends across all of the upper surface 22. As such, the body attachment components 50, 52 and 54 need not be physically separate from one another but can be different areas of a single component or multiple components.

The attachment components 34, 44 that allow the right and left sleeves 30, 40 to be attached to the drape body 14 may be clips, mechanical fasteners, or fabric fasteners such as hook and loop type fasteners. All of the components 34, 44, 50, 52 and 54 may be the same type or some of them may be of one type while others are of different types.

All of the fenestrations 36, 46, 56 and 58 may be provided with a removable sterile clear cover. These covers may be attached to the upper surface 22 through an adhesive. Alternatively, the clear, sterile covers may be attached to the lower surface 24 of the drape body 14. The sterile, clear covers function to maintain a sterile environment while simultaneously allowing visualization of the various access sites during the procedure without needing to be removed. In use, the healthcare provider may remove the sterile, clear covers from the drape body 14 in order to access the patient at the various locations. Alternatively, the sterile, clear covers may be cut through during the medical procedure and thus left in place while still allowing access to portions of the patient 12 such as the radial arteries 74, 80 and femoral arteries 88, 90. Also, the clear covers may be folded over from the outer surface 22 to affix an edge of a fenestration at the site of the vessel after the proper location of the vessel is confirmed with the drape 10 in place.

The surgical drape 10 may be a four-sight angiography drape that is a sterile device providing for four separate access openings in the four fenestrations 36, 46, 56 and 58 for the left and right femoral arteries 90, 88 and the left and right radial arteries 80, 74. Any one of these fenestrations 36, 46, 56 and 58 can be used as desired to provide access during a catheterization procedure. The surgical drape 10 may be used to drape all four of these sites 74, 80, 88 and 90 of the patient 12 prior to initiating the catheterization procedure so that the healthcare provider has the option of changing the access site that is utilized without repeat sterile preparation of an alternate site. In this regard, the surgical drape 10 gives the healthcare provider the option of using different access sites immediately without having to conduct additional preparation thus saving time and cost in the overall procedure. The drape body 14, sleeves 30, 40 and mittens 32, 42 are all sterile and permit maintenance of sterility if the various components come into contact with one another during the surgical procedure. Intravenous lines may be placed through the fenestrations 36, 46, 56 and 58, or at other access sites in the sleeves 30, 40 or body 14 of the drape.

The sleeves 30, 40 may have buttons, snaps or hook and loop type fasteners along their length to allow access through the sleeves 30, 40 for intravenous lines in either one of the arms 70, 76. This access may be obtained without interference with the procedure regardless of its approach. The buttons, snaps or hook and loop type fasteners may allow the sleeves 30, 40 to be removed at any time during or following completion of the procedure without interfering with the intravenous lines in the arms 70 or 76. As such, when the arms 70, 76 are inserted into the sleeves 30, 40 before or during the surgical procedure, they need not be removed out of the proximate ends of the sleeves 30, 40 that are located at the drape body 14. Instead, the aforementioned buttons, snaps or hook and loop type fasteners along the lengths of the sleeves 30, 40, and the mittens 32, 42 may allow for these components to be opened up to afford or facilitate removal of the sleeves 30, 40 and their components from the arms 70, 76. Alternatively, the buttons, snaps or hook and loop type fasteners along the lateral direction 64 may afford partial removal of the sleeves 30, 40 from the arms 70, 76. These access openings or features may extend along the entire length of the sleeves 30, 40 and mittens 32, 42 from the drape body 14 to the distal terminal ends of the mittens 32, 42 or may extend along the sleeves 30, 40 but terminate at some point prior to the terminal distal ends. If the sleeves 30, 40 have these features, the sleeves 30, 40 may be placed onto the arms 70, 76 and positioned thereon without the patient 12 having to extend his or her arms through the openings at the proximal ends of the sleeves 30, 40.

The surgical drape 10 provides a sterile field and preparation for all commonly utilized arterial and venous access sites such as the right and left femoral areas and the right and left radial areas. The surgical drape 10 allows for access to these sites prior to the healthcare provider initiating the procedure to allow the healthcare provider to both choose the desired access site and to change access sites at any time prior to or during the catheterization procedure, without procedural delay and without the need to re-drape the patient 12.

Although four fenestrations 36, 46, 56 and 58 are shown, it is to be understood that these four fenestrations may not be provided in accordance with other exemplary embodiments. For example, the surgical drape 10 can be arranged so that the right and left femoral blood vessel fenestrations 56 and 58 are not present while the right sleeve fenestration 36 and left sleeve fenestration 46 are in fact present to allow for percutaneous entry to the radial arteries 74, 80. In other arrangements the fenestrations 36, 46 are not present while one or more fenestrations exist in the drape body 14. Further, although described as being used to access the right and left radial arteries 74, 80, the right and left sleeve fenestrations 36, 46 could be positioned along the elbow portion of the sleeves 30, 40 to allow entry to the antecubital vein. Still further, the sleeves 30, 40 are not limited to a single fenestration 36, 46 but multiple fenestrations may be present on the sleeves 30, 40.

The drape body 14 and sleeves 30, 40 may be made from a variety of materials. For example, these components may be made from woven, reusable fabrics, and non-woven disposable fabrics in accordance with various exemplary embodiments. Viewing portions associated with the fenestrations 36, 46, 56 and 58 may be made of a film such as a polyethylene film to allow for ease of viewing and to provide fluid resistance.

Although shown as being made of a single layer, the drape body 14 may be multi-layered and can include components not illustrated in the figures. The drape body 14, along with the sleeves 30, 40, may include a reinforcement panel that is attached to the base sheet or other material making up these components. The reinforcement panel may be absorbent so as to provide additional absorbency to the surgical drape 10 at particular locations that may need this feature during use. The reinforcement panel or other portion of the surgical drape 10 may have a fluid repellant or fluid impervious film layer. The reinforcement layer may be placed around the fenestrations 36, 46, 56 and 58 in order to reinforce these components of the surgical drape 10. The lower surface 24 of the drape body 14 may include an adhesive that can be applied against the skin of the patient 12 in order to more firmly attach and position the fenestrations 56, 58 as needed. A peelable removable layer may be positioned on top of this adhesive so that the adhesive is only applied when positioning the drape body 14. In a similar manner, adhesive may be located around the sleeve fenestrations 36, 46 facing the arms 70, 76 of the patient 12 to more firmly secure and position the fenestrations 36, 46 in the appropriate areas. The adhesive used may be tacky and pressure sensitive and can be of any biologically acceptable material. The use of adhesive may further function to provide a seal around the fenestrations 36, 46, 56 and 58 to more appropriately seal the surgical site to further maintain a sterile environment.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A surgical drape, comprising:
   a drape body having an upper surface, an oppositely disposed lower surface, a forward edge, an oppositely disposed rearward edge, and a centerline extending between the forward edge and the rearward edge;
   a first body attachment component located at a first location on the upper surface of the drape body, the first location being proximate to a right hip of the patient when the drape is positioned on the patient;
   a second body attachment component located at a second location on the upper surface of the drape body, the second location being at the centerline of the drape body;
   a third body attachment component located at a third location on the upper surface of the drape body, the third location being proximate to a left hip of the patient when the drape is positioned on the patient;
a right sleeve extending from the drape body into which a right arm of a patient is located when the drape is positioned on the patient, wherein the right sleeve has a right sleeve fenestration and a right sleeve attachment component, wherein the right sleeve attachment component is attachable to the first body attachment component to attach the right sleeve to the drape body at the first location and is attachable to the second body attachment component to attach the right sleeve to the drape body at the second location; and
a left sleeve extending from the drape body into which a left arm of the patient is located when the drape is positioned on the patient, wherein the left sleeve has a left sleeve attachment component that is attachable to the second body attachment component to attach the left sleeve to the drape body at the second location and is attachable to the third body attachment component to attach the left sleeve to the drape body at the third location.

2. The surgical drape as set forth in claim 1, wherein when the drape is positioned on the patient the right sleeve fenestration is positioned proximate to a right radial artery of the right arm of the patient,
wherein the drape body has a right femoral blood vessel fenestration that is positioned proximate to a right femoral artery of the patient when the drape is positioned on the patient.

3. The surgical drape as set forth in claim 2, wherein the left sleeve has a left sleeve fenestration, and when the drape is positioned on the patient the left sleeve fenestration is positioned proximate to a left radial artery of the left arm of the patient;
wherein the left sleeve has a left mitten located at a terminal end of the left sleeve, wherein a left hand of the patient is located in the left mitten when the drape is positioned on the patient;
wherein the right sleeve has a right mitten located at a terminal end of the right sleeve, wherein a right hand of the patient is located in the right mitten when the drape is positioned on the patient; and
wherein the drape body has a left femoral blood vessel fenestration that is positioned proximate to a left femoral artery of the patient when the drape is positioned on the patient.

4. The surgical drape as set forth in claim 1, wherein the right sleeve attachment component, left sleeve attachment component, first body attachment component, second body attachment component and third body attachment components are made of hook and loop type fasteners such that the right sleeve attachment component is releasably attachable to each of the first and second body attachment components, and the left sleeve attachment component is releasably attachable to each of the second and third body attachment components.

5. A surgical drape, comprising:
a drape body having an upper surface and an oppositely disposed lower surface;
a right sleeve extending from the drape body into which a right arm of a patient is located when the drape is positioned on the patient;
a right sleeve attachment component located on the right sleeve;
a left sleeve extending from the drape body into which a left arm of the patient is located when the drape is positioned on the patient;
a left sleeve attachment component located on the left sleeve;
a first body attachment component located on the drape body at a first location, wherein the right sleeve attachment component is attachable to the first body attachment component to attach the right sleeve to the drape body at the first location;
a second body attachment component located on the drape body at a second location, wherein the right sleeve attachment component is attachable to the second body attachment component to attach the right sleeve to the drape body at a second location, wherein the left sleeve attachment component is attachable to the second body attachment component to attach the left sleeve to the drape body at the second location;
a third body attachment component located on the drape body at a third location, wherein the left sleeve attachment component is attachable to the third body attachment component to attach the left sleeve to the drape body at the third location; and
a fenestration through which a portion of the patient can be accessed when the drape is positioned on the patient.

6. The surgical drape as set forth in claim 5, wherein the first location is proximate to a right hip of the patient when the drape is positioned on the patient, wherein when the right sleeve attachment component is attached to the first body attachment component the right sleeve extends along a right side of the patient in a longitudinal direction when the drape is positioned on the patient;
wherein the third location is proximate to a left hip of the patient when the drape is positioned on the patient, wherein when the left sleeve attachment component is attached to the third body attachment component the left sleeve extends along a left side of the patient in the longitudinal direction when the drape is positioned on the patient;
wherein the second location is proximate to a torso of the patient when the drape is positioned on the patient, wherein when the right sleeve attachment component is attached to the second body attachment component the right sleeve extends right to left across the torso of the patient in a lateral direction when the drape is positioned on the patient;
wherein when the left sleeve attachment component is attached to the second body attachment component the left sleeve extends left to right across the torso of the patient in the lateral direction when the drape is positioned on the patient.

7. The surgical drape as set forth in claim 5, wherein the right and left sleeve attachment components include hooks of a hook and loop type fastener, wherein the first, second and third body attachment components include loops of the hook and loop type fastener.

8. The surgical drape as set forth in claim 5, wherein the attachment between the right sleeve attachment component and each of the first and second body attachment components is releasable attachment such that the right sleeve and the drape body can be attached to and removed from one another a repeated number of times, and wherein the attachment between the left sleeve attachment component and each of the second and third body attachment components is releasable attachment such that the left sleeve and the drape body can be attached to and removed from one another a repeated number of times.

9. The surgical drape as set forth in claim 5, wherein the right and left sleeve attachment components and the first, second and third body attachment components are made of a hook and loop type fastener, wherein the hook and loops type fastener renders the right sleeve attachment component releasably attachable to each of the first and second body attachment components and the left sleeve attachment component releasably attachable to each of the second and third body attachment components.

10. The surgical drape as set forth in claim 5, wherein the left sleeve has a left mitten at a terminal end, wherein a left hand of the patient is located in the left mitten when the drape is positioned on the patient;

wherein the right sleeve has a right mitten at a terminal end, wherein a right hand of the patient is located in the right mitten when the drape is positioned on the patient.

11. The surgical drape as set forth in claim 5, wherein the fenestration is located in one of the right and left sleeves, wherein the fenestration is positioned proximate to a femoral artery of the patient when the drape is positioned on the patient.

12. The surgical drape as set forth in claim 5, further comprising;

a right sleeve fenestration located on the right sleeve and positioned proximate to a right radial artery of the right arm of the patient when the right arm is located in the right sleeve;

a left sleeve fenestration located on the left sleeve, and positioned proximate to a left radial artery of the left arm of the patient when the left arm is located in the left sleeve;

a right femoral blood vessel fenestration located on the drape body and is positioned proximate to the right femoral artery of the patient when the drape is positioned on the patient; and a left femoral blood vessel fenestration located on the drape body and is positioned proximate to the left femoral artery of the patient when the drape is positioned on the patient.

13. The surgical drape as set forth in claim 5, wherein the drape body has a forward edge, an oppositely disposed rearward edge, and a centerline from the forward edge to the rearward edge, wherein the second location is located at the centerline, wherein the first location is spaced a distance from the centerline in a lateral direction, wherein the third location is spaced a distance from the centerline in the lateral direction, wherein the centerline is located between the first location and the third location in the lateral direction.

* * * * *